United States Patent [19]

Sikkenga

[11] Patent Number: 4,990,717

[45] Date of Patent: Feb. 5, 1991

[54] MONOALKENYLATION OF ALKYLBENZENES IN A FIXED CATALYST BED

[75] Inventor: David L. Sikkenga, Wheaton, Ill.

[73] Assignee: Amoco Corporation, Chicago, Ill.

[21] Appl. No.: 438,335

[22] Filed: Nov. 16, 1989

[51] Int. Cl.$^5$ ................................................ C07C 2/72
[52] U.S. Cl. ...................................... 585/429; 585/452
[58] Field of Search ................................ 585/429, 452

[56] References Cited

U.S. PATENT DOCUMENTS

| | | | |
|---|---|---|---|
| 3,244,758 | 4/1966 | Eberhardt | 585/452 |
| 3,865,889 | 2/1975 | Mitchell | 585/452 |
| 3,904,702 | 9/1975 | Mitchell | 585/438 |
| 3,953,535 | 4/1976 | Shima et al. | 585/452 |
| 3,954,895 | 5/1976 | Shima et al. | 585/438 |
| 4,018,840 | 4/1977 | Iwata et al. | 585/452 |

Primary Examiner—Curtis R. Davis
Assistant Examiner—James Saba
Attorney, Agent, or Firm—James R. Henes; William H. Magidson; Ralph C. Medhurst

[57] ABSTRACT

A method for the production of a monoalkenylated benzene is disclosed. In this method an alkylbenzene is reacted with a $C_4$ to $C_5$ conjugated diene in a fixed catalyst bed containing a supported alkali metal catalyst. A monoalkenylated reaction product is produced and is separated from the reactants.

21 Claims, 2 Drawing Sheets

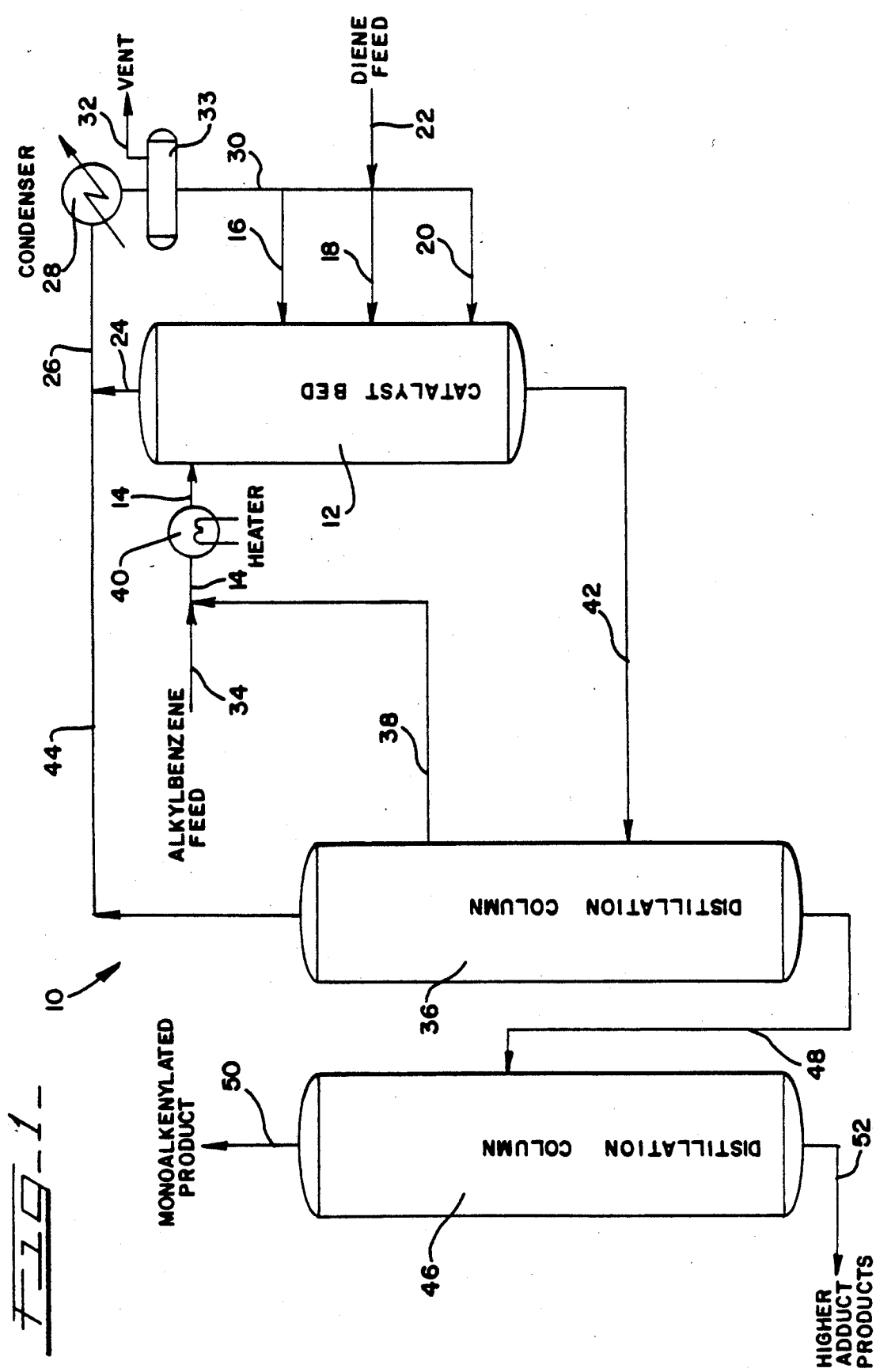

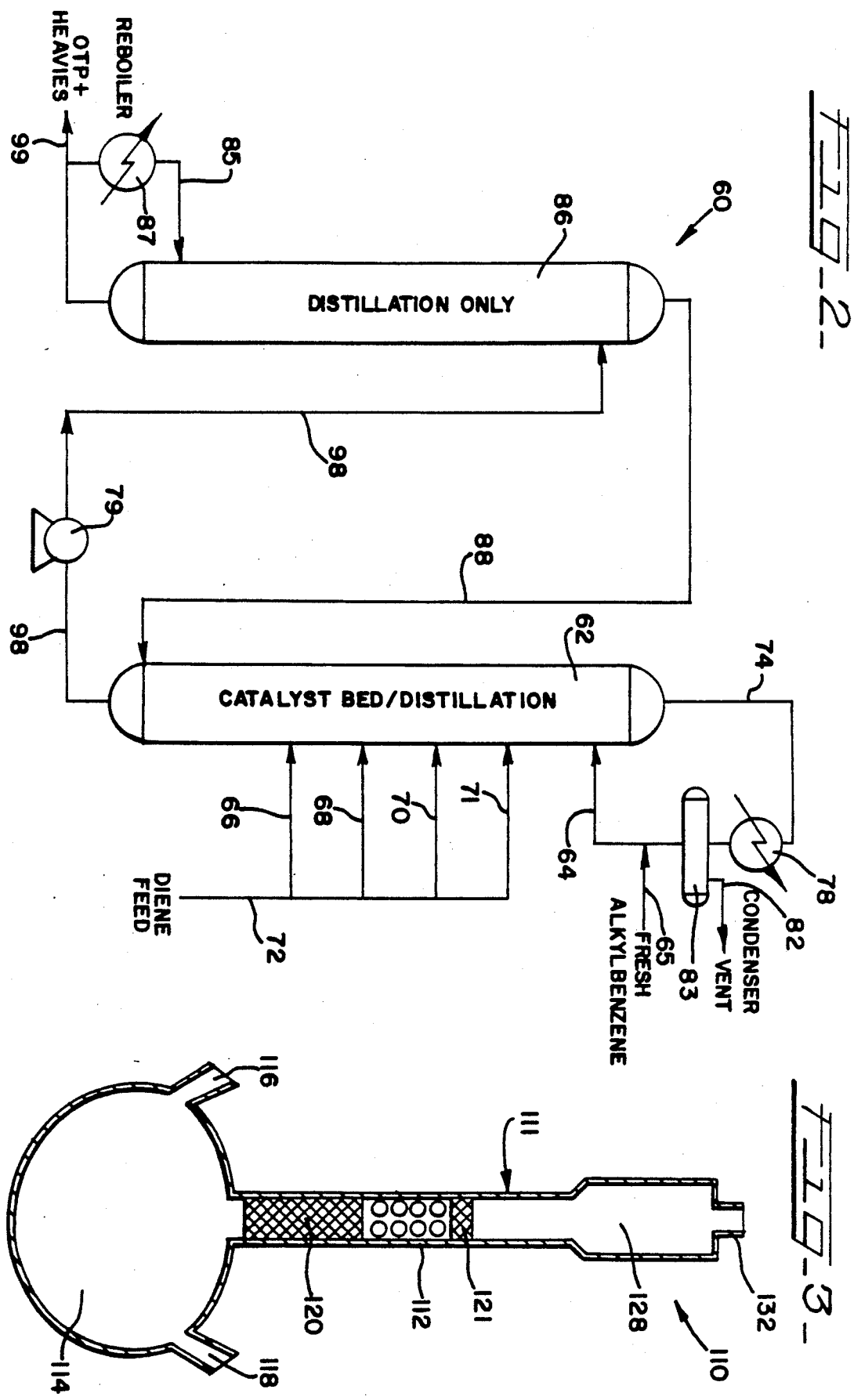

MONOALKENYLATION OF ALKYLBENZENES IN A FIXED CATALYST BED

The present invention relates to a method for producing monoalkenylated benzenes of relatively high purity.

BACKGROUND OF THE INVENTION

The production of alkenylbenzenes by the reaction of alkylbenzenes with conjugated dienes in the presence of an alkali metal catalyst is well known. These reactions, however, are carried out in catalyst slurries at moderate to elevated reaction temperatures. The alkali metal catalyst is slurried with the liquid alkylbenzene, and a conjugated diene is then added to the reaction mixture. See, for example, U.S. Pat. Nos. 3,766,288, 3,953,535, and 3,954,896, to Shima et al; U.S. Pat. Nos. 3,841,844, 3,865,889 and 3,904,702 to Mitchell; U.S. Pat. No. 1,934,123 to Hofmann et al.; U.S. Pat. No. 4,018,840 to Iwata et al.; and Teijin, Ltd. U.K. Pat. Nos. 1,390,874 and 1,483,426.

The prior methodologies have the disadvantage that often two or more alkenyl groups are added to the alkylbenzene because additional conjugated diene present continues to react with the initial reaction product. Moreover, the catalyst has to be recovered from the reaction mixture.

The method of the present invention overcomes this difficulty by separating the monoalkenylated benzene from the catalyst substantially as soon as it is produced, thus preferentially producing the monoalkenylated product at relatively high purity.

SUMMARY OF THE INVENTION

The present invention contemplates a method for the production of a monoalkenylated benzene wherein an alkylbenzene is reacted with a $C_4$ to $C_5$ conjugated diene in a fixed catalyst bed containing a supported alkali metal catalyst to produce a monoalkenylated benzene, a commercially valuable starting material precursor for the manufacture of polyester resins. Within the catalyst bed the process temperature is controlled so that the alkylbenzene preferably is present as a mixed phase, i.e., gaseous alkylbenzene in equilibrium with liquid alkylbenzene.

Mono-alkenylated reaction product generated in the catalyst bed is separated from any unreacted alkylbenzene and/or $C_4$ to $C_5$ conjugated diene that may be present. The separation can be effected within the catalyst bed, upstream therefrom, or downstream therefrom, as desired. Unreacted alkylbenzene and conjugated diene obtained in the foregoing manner can be recycled to the catalyst bed for continuation of the alkenylation reaction.

In a preferred method embodiment of the present invention, an admixture of o-xylene and gaseous 1,3-butadiene is fed to the fixed catalyst bed and contacted with potassium metal supported on alumina to produce 5-(o-tolyl)-2-pentene, which is then recovered from the effluent stream or separated out within the catalyst bed. 5-(o-Tolyl)-2-pentene, in turn, when cyclized, dehydrogenated and oxidized, can be converted to naphthalene dicarboxylic acid, a starting material for polyester resin production.

In practicing the present invention, the monoalkenylated benzene reaction product is continuously removed from the catalyst bed following the initial alkenylation reaction. Such removal of the reaction product substantially precludes further alkenylation of the produced monoalkenylated benzene by reaction with additional $C_4$ to $C_5$ conjugated diene. Thus, a monoalkenylated benzene is preferentially produced in a relatively high yield.

BRIEF DESCRIPTION OF DRAWINGS

In the drawings, FIG. 1 is a schematic illustration of a system suitable for practicing the process of the present invention.

FIG. 2 is a schematic illustration of another continuous system suitable for practicing the present invention; and FIG. 3 is a schematic illustration of a batch system suitable for practicing this invention.

DESCRIPTION OF PREFERRED EMBODIMENTS

A mixed phase alkenylation of an alkylbenzene with a $C_4$ to $C_5$ conjugated diene in the presence of a supported alkali metal catalyst in a fixed bed is contemplated by the present method.

Suitable alkylbenzenes for the present purpose are substituted benzenes having substituted thereon at least one alkyl radical of one or two carbon atoms. Such compounds can be represented by the formula

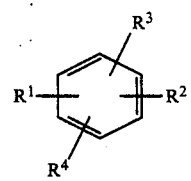

wherein $R^1$ is an alkyl radical of one or two carbon atoms, and $R^2$, $R^3$ and $R^4$, which may be the same or different, are each hydrogen or an alkyl radical of one to three carbon atoms.

Illustrative of such alkylbenzenes are toluene, the xylenes, ethylbenzene, trimethylbenzene, tetramethylbenzene and the like. Preferred as starting materials for the present method are the xylenes, i.e., o-xylene, m-xylene and p-xylene, as well as ethylbenzene.

In practicing the present method the alkylbenzenes can be used either singly or as mixtures of two or more thereof.

Suitable conjugated dienes for practicing the present method are the $C_4$ to $C_5$ conjugated alkadienes such as 1,3-butadiene, 1,3-pentadiene and isoprene.

Thus, for example, the addition of butadiene to toluene yields 5-phenyl-2-pentene which can be converted by cyclodehydrogenation to 1-methylnaphthalene; the addition of butadiene to o-xylene yields 5-(o-tolyl)-2-pentene which can be similarly converted to 1,5-dimethylnapthalene; the addition of butadiene to p-xylene yields 5-(p-tolyl)-2-pentene which can be similarly converted to 1,7-dimethylnaphthalene; the addition of butadiene to ethylbenzene yields 5-phenyl-2-hexene which can be similarly converted to 1,4-dimethylnaphthalene, etc.

The alkenylation reaction is catalyzed by an alkali metal, i.e., a metal of Group IA of the Periodic Table of Elements such as sodium, potassium, lithium, rubidium, cesium, as well as mixtures or alloys thereof. Potassium and sodium are particularly preferred for the present purposes and can be used either singly or in combination. The alkali metal catalyst is supported on a particulate inorganic carrier such as alumina, silica, zeolites, silicon carbide, graphite, inorganic bases of the elements of Groups IA, IIA, and IIIB of the Periodic Table of Elements (e.g., sodium oxide, potassium oxide, calcium oxide, barium oxide, potassium carbonate, sodium carbonate etc.), and the like. A promoter such as bromobenzene may also be present. Illustrative such catalysts are described in Pham Van Thong et al., Neftekhimija 21(2):205-208 (1981) and in Dimitrov et al., Dokl. Bolg. Akad. Nauk. 33(3):353-355(1980).

In accordance with the present method, the alkali metal catalyst on a suitable carrier is positioned as a fixed porous bed through which the alkenylation reactants are then passed. In a continuous process the weight hourly space velocity (WHSV; weight of feed/hour/weight of catalyst) usually is in the range of about 0.1 hr$^{-1}$ to about 4 hr$^{-1}$, preferably about 0.2 hr$^{-1}$ to about 2 hr$^{-1}$. For the $C_4$ to $C_5$ conjugated diene in the continuous process the WHSV usually is in the range of about 0.1 hr$^{-1}$ to about 3 hr$^{-1}$, and preferably in the range of about 0.1 hr$^{-1}$ to about 1 hr$^{-1}$. The temperature in the fixed catalyst bed preferably is maintained at about the boiling point of the alkylbenzene reactant so that a liquid/vapor equilibrium for the alkylbenzene reactant exists within the fixed catalyst bed. However, the temperature in the fixed catalyst bed must not exceed the boiling point of the produced monoalkenylated product.

The alkali metal concentration on the inorganic support or carrier can be in the range of about 0.5 to about 25 percent by weight of catalyst.

The alkylbenzenes contemplated as reactants are normally liquid, and thus can be pre-heated in any convenient manner if additional heat input to the catalyst bed is desired. The alkylbenzenes can be admixed with the $C_4$ to $C_5$ conjugated diene in the catalyst bed in gaseous as well as in liquid state inasmuch as the diene is soluble in the alkylbenzene, and thus a liquid phase as well as a gas phase alkenylation can be effected. By the same token, by maintaining a gas/liquid equilibrium in the reaction zone, a liquid phase reaction can be carried out concurrently with a gas phase reaction. The alkenylation reaction is exothermic, thus external heat input may not always be required. The alkenylated product is recovered from the catalyst bed either directly or from the effluent therefrom upstream or downstream from the catalyst bed, depending upon the process embodiment employed.

The relative amounts of the alkylbenzene and the conjugated diene in the feed to the catalyst bed can vary over a relatively wide range. However, it is preferable to maintain a stoichiometric excess of the alkylbenzene in the catalyst bed. In this manner the likelihood of diene homopolymerization with attendant formation of an undesirable rubbery substance on the catalyst can be minimized.

Preferably, the mole ratio of alkylbenzene to the conjugated diene in the supported alkali metal catalyst bed is in the range of about 2:1 to about 100:1, more preferably about 5:1.

Inasmuch as water and oxygen can react with the alkali metal that is present in the particulate catalyst, preferably the reactant feed stream to the catalyst is substantially dry and free from oxygen.

The alkenylation reaction of the present invention can be effected as a batch or as a continuous process, and is preferably carried out at a temperature of about 80 degrees C. to about 200 degrees C. and under an absolute pressure of about 0.1 atmospheres to about 10 atmospheres.

In the illustrative embodiment shown in FIG. 1, alkenylation system 10 suitable for practicing the present invention includes a fixed catalyst bed 12 that receives an alkylbenzene feed from conduit 14 and a diene feed via one or more of conduits 16, 18 and 20. Fresh diene feed is introduced into the system from an appropriate source by means of feed conduit 22. Additionally, unreacted diene from catalyst bed 12 exiting via conduit 24 and fed to condenser 28 via conduit 26 can be liquified and returned to catalyst bed 12 through conduit 30. Non-condensable effluent from condenser 28 is separated in gas-liquid separator 33 and is vented via vent line 32.

Fresh alkylbenzene feed from an appropriate source is fed to catalyst bed 12 through conduit 34, is commingled with an alkylbenzene feed stream recovered in distillation column 36, and conveyed to catalyst bed 12 through conduit 38. The resulting, commingled alkylbenzene feed stream enters conduit 14. If necessary a feed pre-heater such as heater 40 can be provided in conduit 14 to elevate the temperature of the alkylbenzene feed stream entering catalyst bed 12.

Monoalkenylated product together with relatively heavier adduct by-products as well as with dissolved diene is removed from catalyst bed 12 and is passed to downstream distillation column 36 through conduit 42. This admixture of reactants and reaction products undergoes a preliminary separation in distillation column 36 so that unreacted reactants can be returned to catalyst bed 12. To that end, diene recovered in distillation column 36 is passed to condenser 28 via conduits 44 and 26, while recovered alkylbenzene is returned via conduit 38 as mentioned hereinabove.

The bottoms stream from distillation column 36, constituted primarily by the monoalkenylated product and higher adduct products, undergoes further separation in product recovery distillation column 46 which receives the bottoms stream from column 36 through conduit 48. The monoalkenylated product exits distillation column 46 via product conduit 50 while the relatively higher adduct products are removed from column 46 through bottoms conduit 52.

In the embodiment of this invention illustrated in FIG. 2, catalytic distillation, and thus at least partial separation of the reactants and reaction products, is initiated and carried out within the catalyst bed. To that end, alkenylation system 60 includes a combined fixed catalyst bed and distillation column 62 that receives an alkylbenzene feed via conduit 64 and recycled alkylbenzene vapor via conduit 88. The feed stream provided via conduit 64 includes fresh alkylbenzene entering the system through conduit 65 as well as recycled alkylbenzene from separator 83 downstream from reflux condenser 78. A diene feed enters system 60 from a suitable source by means of feed conduit 72 and is distributed into catalyst bed 62 via diene feed lines 66, 68, 70 and 71.

Unreacted diene distilled from the mixture of reactants and reaction products present exits catalyst bed 62 through conduit 74 and is recycled back to catalyst bed 62 through reflux condenser 78 via conduit 64. Non-condensable effluent is vented via vent line 82.

The alkenylated products together with unreacted alkylbenzene exit catalyst bed 62 through bottoms conduit 98 and are pumped by pump 79 to downstream distillation column 86 in which the unreacted alkylbenzene is separated from the alkenylated reaction product and is returned to catalyst bed 62 through vapor return conduit 88. Distillation column 86 is further equipped with reboiler 87 which communicates with column 86 via line 85. The alkenylated products are removed from distillation column 86, and thus alkenylation system 60 through conduit 99.

A batch alkenylation system is illustrated in FIG. 3. In this particular instance, system 110 includes heated flask 114 suitable for containing an alkylbenzene and provided with diene feed ports 116 and 118. Particulate catalyst bed 112 is contained within column 111 and is held in place by packing material layers 120 and 121 such as stainless steel packing, or the like. A reflux condenser is situated above catalyst bed 112 and in communication therewith. Non-condensables are vented through vent means 132. Alkenylated products are collected in flask 114 upstream from particulate catalyst bed 112 and subsequently recovered therefrom.

In a preferred embodiment of a batch process, o-xylene is heated to its gaseous state and admixed with 1,3-butadiene. The gaseous mixture is then passed through a porous bed of potassium metal on alumina, which catalyzes the formation of 5-(o-tolyl)-2-pentene. Some of the o-xylene present condenses within the bed. Moreover, separation of reactants and reaction products is initiated within the catalyst bed as well due to the exothermic nature of the alkenylation reaction. The product effluent stream is then passed to a collector where the 5-(o-tolyl)-2-pentene is separated from the unreacted o-xylene and 1,3-butadiene which reactants are then recirculated for reuse. In a particularly preferred embodiment, the collector is a condenser which separates the liquified o-xylene and 5-(o-tolyl)-2-pentene from the unreacted 1,3-butadiene. The reaction product is then separated and recovered by distillation.

The present invention is further illustrated by way of the following EXAMPLES which are not to be taken as limiting in any way.

EXAMPLE 1 Comparison of Stirred Tank and Catalytic Distillation Systems

Dried, reagent grade o-xylene (80–87 grams) was added to a reaction vessel, and reacted with 1,3-butadiene in either a stirred tank reactor or in a heated flask fitted with a fixed catalyst bed and a downstream condenser to effect a catalytic distillation procedure.

A. In the stirred tank procedure, 20 weight percent potassium metal on alumina (10.2 grams) was mixed with the o-xylene in the reaction vessel. The reaction vessel was then heated to 145 degrees C. and the butadiene introduced into the reaction vessel at a rate of 77 ml/min (0.18 mol/hr) over a period of 7 hours, with continuous stirring of the reaction mixture. Samples were taken and analyzed at 2, 4 and 7 hours, respectively, of the reaction. The samples taken correspond to Samples 1, 2 and 3, respectively, in TABLE 1, below.

B. In carrying out the present catalytic distillation procedure, a batch system substantially as shown in FIG. 3 was utilized o-Xylene in the flask was heated to 145 degrees C. The reaction system was first purged with nitrogen and then 1,3-butadiene was introduced into the reaction vessel head space at a rate of 79 ml/min (0.19 mol/hr) The gaseous mixture of o-xylene and 1,3-butadiene was then passed through a packed column containing 20 weight percent potassium metal on alumina (about 9.4 grams) for about 8.5 hours. During this time period the o-xylene effluent vapor was condensed and was returned to the column as reflux. The liquid product was collected in the flask below the column. The temperature in the catalyst bed was noted to be about 139–143 degrees C. during the reaction. The effluent gas stream was collected, containing a total of 24 liters of unreacted 1,3-butadiene. Samples of the effluent gas were collected at 1, 4.5, 7 and 8.5 hours, respectively and analyzed. The collected samples correspond to Samples 4 to 7, respectively, in Table I, below.

TABLE I

| SAMPLE | Conversion and Selectivity Comparisons | | | | | | |
|---|---|---|---|---|---|---|---|
| | 1 | 2 | 3 | 4 | 5 | 6 | 7 |
| REACTOR TYPE | STIRRED TANK | | | CATALYTIC DISTILLATION | | | |
| CATALYST | 20 weight percent K on Al$_2$O$_3$ | | | 20 weight percent K on Al$_2$O$_3$ | | | |
| TEMP, DEGREES C. | 146 | 145 | 143 | 143 | 139 | 141 | 142 |
| HOURS OF RXN | 2 | 4 | 7 | 1 | 4.5 | 7 | 8.5 |
| COMPOSITION-WT % | | | | | | | |
| XYLENE | 64.0 | 46.3 | 33.6 | 90.2 | 69.7 | 48.1 | 39.0 |
| OTP | 9.9 | 19.7 | 17.6 | 5.7 | 16.2 | 26.7 | 30.8 |
| HEAVIES | 23.9 | 32.2 | 45.5 | 3.3 | 12.3 | 22.2 | 28.6 |
| CONVERSION AND SELECTIVITIES | | | | | | | |
| % XYLENE CONV. | 22.4 | 38.5 | 50.4 | 5.7 | 19.5 | 37.3 | 47.0 |
| % C4 TO OTP | 21.8 | 29.0 | 20.5 | 53.5 | 46.9 | 44.6 | 41.9 |
| % oX TO OTP | 35.7 | 45.0 | 34.0 | 69.7 | 63.9 | 61.7 | 59.1 |

TABLE I shows the composition of the samples at the respective assay times for unreacted o-xylene ("xylene"), 5-(o-tolyl)-2-pentene (OTP) and multi-alkenylated product ("Heavies"). The percentage of initially present o-xylene converted, the percent conversion of butadiene to OTP and the percent conversion of o-xylene to OTP is also illustrated. It will be noted that there is a 15 to 20 % increase in the selective conversion of butadiene to OTP using the catalytic distillation process.

EXAMPLE 2 Catalytic Distillation Reaction Utilizing Potassium Metal on Potassium Carbonate A catalytic bed comprised of 8 weight percent potassium metal immobilized on K$_2$CO$_3$ was packed into a distillation column attached to a heated flask as used in EXAMPLE 1B above. Dry, reagent grade o-xylene (80 grams) was heated in the flask that served as the reaction vessel to 145 degrees C., and the reaction system was purged with nitrogen to remove oxygen from the system. 1,3-Butadiene was then added at a rate of 79 ml/min.

The gaseous mixture of o-xylene and 1,3-butadiene was then fed into the packed distillation column, where the alkenylation reaction occurred. The temperature in the catalyst bed was 139–143 degrees C. during the reaction. The o-Xylene effluent was condensed at the top of the column and returned to the column as reflux. The reaction products were collected in the heated flask. The contents of the flask were analyzed at 1, 2, 5, 8 and 10 hours, respectively. The results are illustrated in TABLE II, below and show that the selectivity of butadiene conversion to 5-(o-tolyl)-2-pentene ranges from 65-70% over a wide o-xylene conversion range.

TABLE II

| | Catalytic Distillation Reaction | | | | |
|---|---|---|---|---|---|
| SAMPLE | 8 | 9 | 10 | 11 | 12 |
| CATALYST | 8 weight percent K on $K_2CO_3$ | | | | |
| TEMP, DEGREES C. | 142 | 142 | 142 | 142 | 142 |
| HOURS OF RXN | 1 | 2 | 5 | 8 | 10 |
| COMPOSITION-WEIGHT PERCENT | | | | | |
| XYLENE | 98.5 | 97.2 | 86.2 | 70.3 | 58.7 |
| OTP | 0.6 | 1.8 | 10.4 | 22.4 | 30.2 |
| HEAVIES | 0.2 | 0.5 | 3.0 | 6.9 | 10.8 |
| CONVERSION AND SELECTIVITIES | | | | | |
| % XYLENE CONV. | 0.5 | 1.5 | 8.9 | 20.6 | 30.1 |
| % C4 TO OTP | 67.4 | 69.5 | 69.8 | 68.3 | 65.2 |
| % oX TO OTP | 80.5 | 82.0 | 82.2 | 81.2 | 78.9 |

EXAMPLE 3 Conventional Stirred Tank Batch Process with Unsupported Catalyst

Potassium metal (0.1 weight percent) was stirred into a solution of o-xylene at about 105–120 degrees C. 1,3-Butadiene was added to the stirred solution. The results of this procedure are illustrated in TABLE III, below, as Samples 13 and 14. It will be noted that the selectivity of conversion of the reactants to OTP rapidly decreases with increasing conversion of the o-xylene.

EXAMPLE 4 Alkenylation of o-Xylene in a Stirred Tank Reactor

Dry o-xylene (about 700 ml) and potassium metal (about 0.33 grams) were placed into a clean, dry glass reactor of 1000 ml capacity. The resulting admixture was stirred with an agitator at 1000 RPM and heated to a temperature of about 106 degrees C. Dry butadiene vapor was then introduced into the head space of the reactor at a rate of about 32 grams/hour for a time period of about 3.5 hours. The reactor temperature was maintained in the range of about 106 degrees C. to about 118 degrees C. The reactor contents were sampled and analyzed by gas chromatography after the aforesaid 3.5-hour period. The analytical results are set forth in Table III, below, as Sample 15. These results indicate that the selectivity of the process of the present invention is better than that of the conventional process that utilizes an unsupported metal catalyst in a stirred tank reactor.

TABLE III

| | Stirred Tank Batch Process | | |
|---|---|---|---|
| SAMPLE | 13 | 14 | 15 |
| CATALYST | K METAL SUSPENSION | | |
| TEMP, DEGREES C. | 105–120 | | 106–118 |
| HOURS OF RXN | 2.8 | 8 | 3.5 |
| COMPOSITION-WT % | | | |
| XYLENE | 76.8 | 65.6 | 60.5 |
| OTP | 20.3 | 26.2 | 27.4 |
| HEAVIES | 2.9 | 8.46 | 10.9 |
| CONVERSION AND SELECTIVITY | | | |
| % XYLENE CONV. | 16.2 | 24.7 | 28.0 |
| % C4 TO OTp | 82.4 | 67.4 | 62.7 |
| % oX TO OTP | 90.3 | 80.6 | 77.1 |
| MOLES/100 GM. PRODUCT | | | |
| oX | 0.72 | 0.62 | 0.57 |
| OTP | 0.13 | 0.16 | 0.17 |
| HEAVIES | 0.01 | 0.04 | 0.05 |
| TOTAL | 0.86 | 0.82 | 0.79 |
| MOLE % | | | |
| oX | 83.76 | 75.27 | 71.89 |
| OTP | 14.67 | 19.92 | 21.60 |
| HEAVIES | 1.57 | 4.81 | 6.42 |
| TOTAL | 100.00 | 100.00 | 100.00 |

The foregoing description and the examples are intended as illustrative and are not to be taken as limiting. Still other variations within the spirit and scope of this invention are possible and will readily present themselves to those skilled in the art.

I claim:

1. A method for the production of a monoalkenylated benzene which comprises the steps of
    contacting an alkylbenzene and $C_4$ to $C_5$ conjugated diene reactant admixture with a fixed, porous catalyst bed containing an alkali metal catalyst on a solid particulate support for a time period sufficient to react said diene with said alkylbenzene to produce a monoalkenylated benzene as reaction product in a mixture of reactants and reaction products wherein the temperature of the catalyst bed is maintained below the boiling point of the monoalkenylated benzene product and at about the boiling point of the alkylbenzene such that an alkylbenzene vapor-liquid equilibrium is maintained within the catalyst bed and wherein separation by distillation of the reactants and reaction products present in said mixture of reactants and reaction products is initiated in said catalyst bed;
    separating said mixture from said catalyst bed and recovering the produced monoalkenylated benzene from said mixture of reactants and reaction products.

2. The method in accordance with claim 1 wherein said alkylbenzene is o-xylene.

3. The method in accordance with claim 1 wherein said diene is 1,3-butadiene.

4. The method in accordance with claim 1 wherein said alkali metal catalyst is potassium and said support is alumina.

5. The method in accordance with claim 1 wherein said alkali metal catalyst is potassium and said support is potassium carbonate.

6. The method in accordance with claim 1 wherein said mixture of reactants and reaction products is recovered upstream of said catalyst bed and the monoalkenylated benzene is then separated from the recovered mixture.

7. The method in accordance with claim 1 wherein said mixture of reactants and reaction products is recovered downstream of said catalyst bed and the monoalkenylated benzene is then separated from the recovered mixture.

8. A method for the production of a monoalkenylated benzene comprising the steps of
(a) feeding an alkylbenzene and a $C_4$ to $C_5$ conjugated diene into a fixed, porous catalyst bed containing an alkali metal catalyst supported on a solid support and maintaining the resulting admixture of the alkylbenzene and the diene in contact with said catalyst bed at an elevated temperature and for a time period sufficient to react said diene with said alkylbenzene to produce a monoalkenylated benzene in a mixture of reactants reaction products, wherein the temperature of the catalyst bed is maintained below the boiling point of the monoalkenylated benzene product and at about the boiling point of the alkylbenzene such that an alkylbenzene vapor-liquid equilibrium is maintained within the catalyst bed and wherein separation by distillation of the reactants and reaction products present in said mixture of reactants and reaction products is initiated in said catalyst bed;
(b) recovering an effluent containing the monoalkenylated benzene together with unreacted alkylbenzene and $C_4$ to $C_5$ conjugated diene from said catalyst bed; and
(c) separating said monoalkenylated benzene from said effluent.

9. The method according to claim 8 wherein unreacted alkylbenzene is recovered from the effluent and is recycled to the catalyst bed.

10. The method according to claim 8 wherein unreacted $C_4$ to $C_5$ conjugated diene is recovered from the effluent and is recycled to the catalyst bed.

11. The method according to claim 8 wherein said alkylbenzene is an ortho-alkyl-substituted toluene.

12. The method according to claim 11 wherein said ortho-alkyl substituted toluene is o-xylene.

13. The method according to claim 8 wherein said diene is 1,3-butadiene.

14. The method according to claim 8 wherein said alkali metal catalyst is selected from the group consisting of potassium, sodium, lithium, cesium and rubidium.

15. The method according to claim 8 wherein said solid support is alumina.

16. The method according to claim 8 wherein said solid support is potassium carbonate.

17. The method according to claim 8 wherein said metal catalyst is potassium metal on alumina.

18. The method according to claim 17 wherein said potassium metal is present in said catalyst in an amount of about 20 weight percent.

19. The method according to claim 8 wherein said catalyst is potassium metal on potassium carbonate.

20. The method according to claim 19 wherein said potassium metal is present in said catalyst in an amount of about 8 weight percent.

21. The method according to claim 8 wherein a stoichiometric excess of the alkylbenzene is maintained within the catalyst bed.

* * * * *

UNITED STATES PATENT OFFICE
CERTIFICATE OF CORRECTION

Patent No. 4,990,717　　　　　　　　　Dated Feb. 5, 1991

Inventor(s) David A. Sikkenga

It is certified that error appears in the above-identified patent and that said Letters Patent is hereby corrected as shown below:

| Col. | Line | |
|---|---|---|
| 6 | 9 | "utilized o-Xylene" should read --utilized.  o-Xylene |
| 6 | 13 | "hr) The" should read --hr).  The-- |
| 9 | 30 | "reactants reaction" should read --reactants and reaction-- |

Signed and Sealed this

Eleventh Day of August, 1992

*Attest:*

DOUGLAS B. COMER

*Attesting Officer*　　　　*Acting Commissioner of Patents and Trademarks*